US007766841B2

(12) United States Patent
Yamamoto et al.

(10) Patent No.: US 7,766,841 B2
(45) Date of Patent: Aug. 3, 2010

(54) SLEEP DIAGNOSIS DEVICE

(75) Inventors: Matsuki Yamamoto, Ashiya (JP); Shogo Fukushima, Moriguchi (JP); Aki Nakatsukasa, Osaka (JP)

(73) Assignee: Panasonic Electric Works Co., Ltd., Kadoma-shi (JP)

( * ) Notice: Subject to any disclaimer, the term of this patent is extended or adjusted under 35 U.S.C. 154(b) by 172 days.

(21) Appl. No.: 11/920,342

(22) PCT Filed: May 17, 2006

(86) PCT No.: PCT/JP2006/309818

§ 371 (c)(1),
(2), (4) Date: Nov. 14, 2007

(87) PCT Pub. No.: WO2006/123691

PCT Pub. Date: Nov. 23, 2006

(65) Prior Publication Data

US 2009/0062628 A1   Mar. 5, 2009

(30) Foreign Application Priority Data

| May 18, 2005 | (JP) | ............................. 2005-145076 |
| Dec. 5, 2005 | (JP) | ............................. 2005-350586 |
| Apr. 21, 2006 | (JP) | ............................. 2006-118491 |

(51) Int. Cl.
  *A61B 5/08* (2006.01)
(52) U.S. Cl. ...................................... 600/534; 600/301
(58) Field of Classification Search ................ 600/529, 600/534–536, 538, 595
  See application file for complete search history.

(56) References Cited

U.S. PATENT DOCUMENTS

| 6,306,088 | B1 * | 10/2001 | Krausman et al. ........... 600/301 |
| 7,471,290 | B2 * | 12/2008 | Wang et al. ................. 345/419 |
| 2002/0118121 | A1 * | 8/2002 | Lehrman et al. ....... 340/870.16 |

(Continued)

FOREIGN PATENT DOCUMENTS

JP   10-118047 A   5/1998

(Continued)

OTHER PUBLICATIONS

Y. Kishimoto et al., "Position presumption during sleeping by using a three-axis acceleration sensor," IEICE Technical Report, Dec. 2, 2005, vol. 105, No. 456, pp. 45-48.

(Continued)

*Primary Examiner*—Charles A Marmor, II
*Assistant Examiner*—Carrie Dorna
(74) *Attorney, Agent, or Firm*—Edwards Angell Palmer & Dodge LLP

(57) ABSTRACT

The sleep diagnosis device 1 of the present invention comprises three-dimensional acceleration sensors 2a and 2b, a posture detector 5 which detects a posture of the patient from a DC component of the three-dimensional acceleration sensors, and a breathing movement detector 4 which detects a breathing movement of the patient from the AC component of the three-dimensional acceleration sensors. The sleep diagnosis device of the present invention can detect the posture (sleeping posture) and the breathing movement of the patient by using one three-dimensional acceleration sensor, so it is possible to reduce the number of sensors. Furthermore, the sleep diagnosis device can detect the breathing movement accurately by the three-dimensional acceleration sensors.

11 Claims, 9 Drawing Sheets

U.S. PATENT DOCUMENTS

| | | |
|---|---|---|
| 2005/0027216 A1 | 2/2005 | Guillemaud et al. |
| 2005/0206518 A1 | 9/2005 | Welch et al. |
| 2006/0238333 A1 | 10/2006 | Welch et al. |
| 2007/0013511 A1 | 1/2007 | Weiner et al. |
| 2007/0032732 A1 | 2/2007 | Shelley et al. |
| 2007/0069887 A1 | 3/2007 | Welch et al. |

FOREIGN PATENT DOCUMENTS

| | | |
|---|---|---|
| JP | 2000-271103 A | 10/2000 |
| JP | 2001-327482 | 11/2001 |
| JP | 2002-065640 A | 3/2002 |
| JP | 2003-265439 A | 9/2003 |
| JP | 2004-081632 A | 3/2004 |
| JP | 2004-089267 A | 3/2004 |
| JP | 2005-034364 | 2/2005 |
| JP | 2005-066323 | 3/2005 |
| JP | 2005-230511 | 9/2005 |
| WO | WO 2004/084720 A2 | 10/2004 |

OTHER PUBLICATIONS

Office Action dated Dec. 1, 2009, issued for the Japanese Application No. 2006-182693 and English translation thereof.

Office Action dated Dec. 1, 2009, issued for the Japanese Application No. 2006-182694 and English translation thereof.

* cited by examiner

SLEEP DIAGNOSIS DEVICE

BACKGROUND OF THE INVENTION

1. Field of the Invention

The present invention relates to a sleep diagnosis device which is used for diagnosing sleep apnea syndrome (SAS) and so on.

2. Description of the Related Art

In recent years, there have been a lot of social concerns in sleep apnea syndrome. In a test for sleep apnea syndrome, many sensors, such as temperature sensors for detecting breath from the nose and mouth, a tracheal sound sensor for detecting a snore, a respiration sensor for measuring a breathing movement, a body position sensor for detecting a posture of a patient, and a heart beat sensor for measuring heartbeat, are used.

In a conventional inspection apparatus for sleep apnea syndrome, in order to measure a breathing movement of a patient, strain gauges in a form of a band are wrapped around a chest and a belly (abdomen), and a phase difference between a motion of the chest and a motion of the belly and a magnitude of these motions are measured, and based on the measurement result and a detection result of the breath from the nose and mouth, a type of apnea, for example, central apnea or obstructive apnea, is judged. Or, in another inspection apparatus, pressure sensors are attached to a chest and a belly of a patient to measure a breathing movement of the patient.

Therefore, such a conventional inspection apparatus is burdensome for a patient to whom various sensors are attached, so it is expected to reduce the number of sensors as much as possible and to ease the burden of the patient.

By the way, Japanese Non-examined Patent Publication No. 2005-230511 discloses a sleep apnea syndrome control device. In this device, one-dimensional acceleration sensors are attached to a chest and a belly of a patient to detect a breathing movement of the patient.

However, because motions of the chest and the belly by a breathing movement vary from person to person, an evaluation of the breathing movement based on the acceleration of one direction was inadequate. Furthermore, in the above invention, it is necessary to separately prepare a pressure-sensitive sheet on a mat to detect a posture (a sleeping posture) of the patient.

DISCLOSURE SUMMARY OF THE INVENTION

In view of the above problem, the object of the present invention is to provide a sleep diagnosis device capable of easing the burden of the patient by reducing the number of sensors and detecting the breathing movement of the patient accurately.

The sleep diagnosis device of the present invention comprises a three-dimensional acceleration sensor, a posture detector configured to detect a posture of a patient from a DC component of the three-dimensional acceleration sensor, and a breathing movement detector configured to detect a breathing movement of the patient from an AC component of the three-dimensional acceleration sensor.

Because the sleep diagnosis device of the present invention can detect the posture (sleeping posture) and the breathing movement of the patient by using one three-dimensional acceleration sensor, it is not necessary for the sleep diagnosis device of the present invention to separately prepare a body position sensor for detecting a posture of a patient and a respiration sensor for detecting a breathing movement of the patient, whereby it is possible to reduce the number of sensors and ease the burden of the patient. Furthermore, because the sleep diagnosis device of the present invention detects the breathing movement by the three-dimensional acceleration sensor, it is possible to detect the breathing movement accurately in response to the movement of the chest and the belly of the patient in various directions.

Preferably, the breathing movement detector includes a one-dimensional converting means configured to generate one-dimensional acceleration data from the three-dimensional acceleration data obtained by the three-dimensional acceleration sensor, an inflection point detecting means configured to detect inflection points of a variation of the one-dimensional acceleration data from the one-dimensional acceleration data generated by the one-dimensional converting means, and a breathing movement calculating means configured to calculate the breathing movement of the patient from the inflection points of the variation of the one-dimensional acceleration data obtained by the inflection point detecting means.

In this case, it is possible to detect the breathing movement of the patient accurately from the output of the three-dimensional acceleration sensor.

More preferably, the one-dimensional converting means comprises a principal axis calculating means configured to calculate a principal axis of the variation of the acceleration from the three-dimensional acceleration data obtained by the three-dimensional acceleration sensor, and a one-dimensional data generating means configured to generate the one-dimensional acceleration data by projecting the three-dimensional acceleration data onto the principal axis calculated by the principal axis calculating means.

In this case, it is possible to generate the one-dimensional acceleration data which takes a variation of the principal axis of the acceleration, that is, a principal direction of the movement, into account, and it is possible to obtain the one-dimensional acceleration data in which the variation of the acceleration is accurately reflected.

It is preferable that the principal axis calculating means is configured to calculate an approximate plane from the three-dimensional acceleration data and to generate a two-dimensional acceleration data by projecting the three-dimensional acceleration data onto the approximate plane and to calculate an approximate line from the two-dimensional acceleration data, and the one-dimensional data generating means is configured to use the approximate line calculated by the principal axis calculating means as a principal axis and to generate the one-dimensional acceleration data by projecting the two-dimensional acceleration data onto the principal axis.

Or, the principal axis calculating means may be configured to calculate an approximate line by using the three-dimensional acceleration data, and the one-dimensional data generating means may by configured to use the approximate line calculated by the principal axis calculating means as a principal axis and to generate the one-dimensional acceleration data by projecting the three-dimensional acceleration data onto the principal axis.

Preferably, the breathing movement calculating means includes a breathing rate calculating means configured to calculate a breathing rate of the patient per unit of time by using a time difference between a certain convex inflection point and the next convex inflection point or a time difference between a certain concave inflection point and the next concave inflection point, out of the inflection points of the variation of the one-dimensional acceleration data.

In this case, it is possible to detect the breathing rate of the patient accurately.

Preferably, the breathing movement calculating means includes an apnea detecting means configured to detect an interval between adjacent inflection points of the variation of the one-dimensional acceleration data as an apnea interval if a time difference between the adjacent inflection points is greater than a criterion value.

In this case, it is possible to detect the apnea interval of the patient accurately.

More preferably, the breathing movement calculating means further includes an apnea period detecting means configured to get a start time of the apnea interval as a breathing stop time and get a stop time of the apnea interval as a breathing start time when the apnea detecting means detects the apnea interval.

Preferably, the breathing movement detector includes a breathing strength calculating means configured to calculate strength of the breath by using intensity difference between adjacent inflection points of the variation of the one-dimensional acceleration data.

In this case, it is possible to detect the strength of the breath of the patient accurately.

Preferably, when the x-axis direction is defined as a left-right direction of the patient and the y-axis direction is defined as a body height direction of the patient and the z-axis direction is defined as a thickness direction of the patient, the posture detector calculates a trunk angle of the patient from each component DCy and DCz of the DC component of the three acceleration sensor in a y-axis and a z-axis directions, and calculates a sleeping posture angle of the patient from each component DCx and DCz of the DC component of the three acceleration sensor in a x-axis and z-axis directions.

In this case, it is possible to detect the trunk angle and the sleeping posture angle of the patient from the three-dimensional acceleration sensor, whereby it is possible to detect the posture (sleeping posture) of the patient accurately. As will hereinafter be described in detail, when the x-axis direction is defined as a left-right direction of the patient and the y-axis direction is defined as a body height direction of the patient and the z-axis direction is defined as a thickness direction of the patient, the trunk angle means an angle between the Y-axis direction and the horizontal direction, and the sleeping posture angle means an angle between the Z-axis direction and the normal direction of the horizontal plane.

Preferably, the sleeping diagnosis device further comprises a heart rate detector configured to detect a heart rate of the patient from the AC component of the three-dimensional acceleration sensor.

In this case, it is possible to detect the heart rate of the patient from the three-dimensional acceleration sensor in addition to the posture and the breathing movement of the patient, whereby it is possible to reduce the number of sensors and to ease the burden of the patient.

The heart rate detector can detect the heart rate of the patient by filtering a component ACz of the AC component of the three dimensional acceleration sensor in a z-axis direction by a band-pass filter and calculating an inverse of a peak period of the filtered component ACz.

DETAILED DESCRIPTION OF AN EXEMPLARY EMBODIMENT

Hereinafter, the present invention will be described in more detail with reference to the accompanying drawings.

A sleep diagnosis device 1 in accordance with an embodiment of the present invention is used for a test of, for example, sleep apnea syndrome, and it is configured to evaluate sleep apnea syndrome by using mainly apnea-hypopnea index (AHI). The AHI is a value showing the number of events of apnea or hypopnea per hour of sleep, and an AHI of 5-14 is diagnosed as mild, an AHI of 15-29 is diagnosed as moderate, and an AHI which is equal to or more than 30 is diagnosed as severe.

Figure 1:
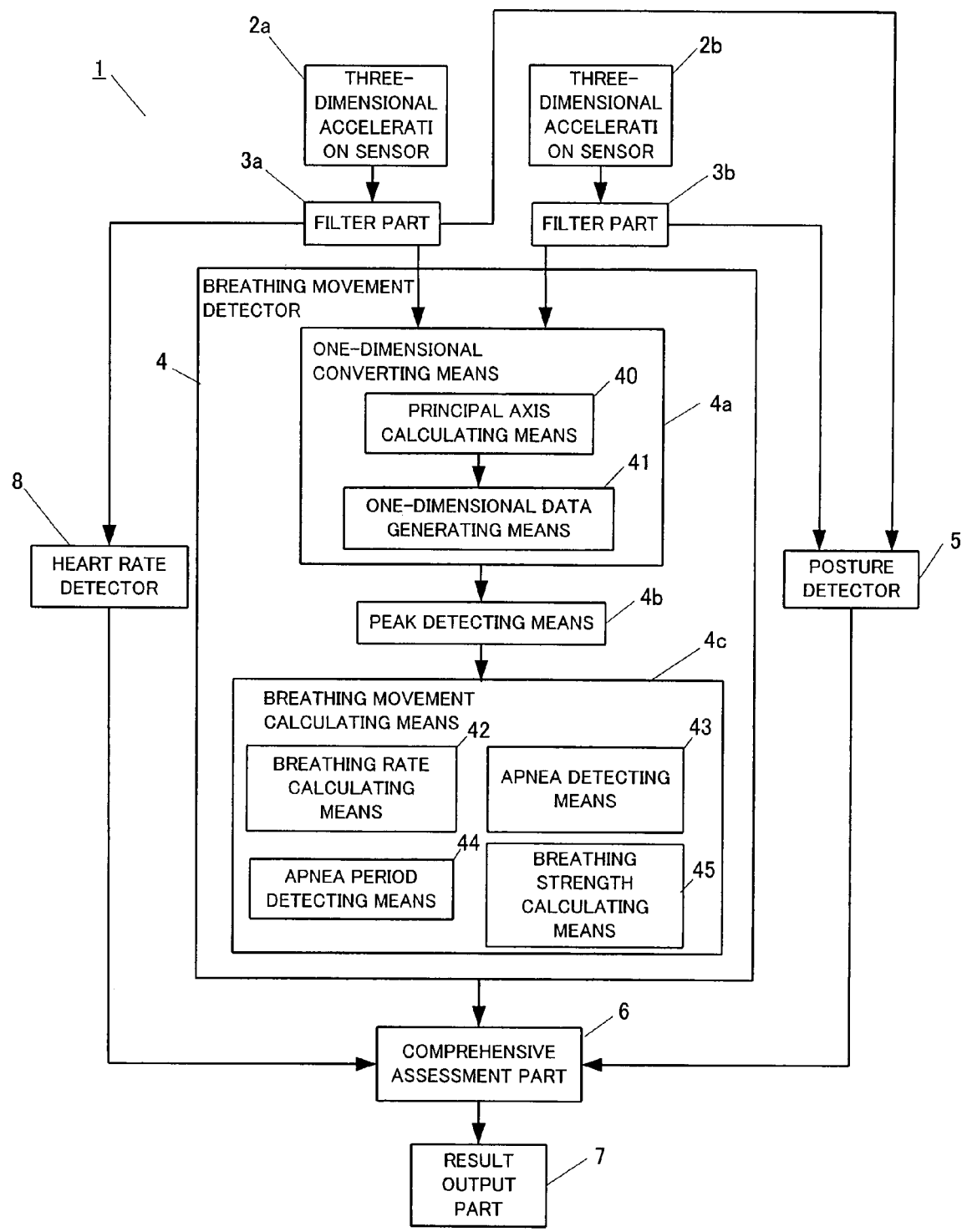
FIG. 1 is a block diagram of a sleep diagnosis device in accordance with an embodiment of the present invention.

As shown in FIG. 1, the sleep diagnosis device 1 comprises three-dimensional acceleration sensors (triaxial acceleration sensors) 2a and 2b which are attached to a body of a patient H (see FIGS. 2A and 2B), filter parts 3a and 3b for extracting an alternating-current component (AC component) and a direct-current component (DC component) from an output of each of the acceleration sensors 2a and 2b, a breathing movement detector 4 for detecting a breathing movement of the patient from the AC component of each three-dimensional acceleration sensor 2a and 2b, a posture detector 5 for detecting a posture of the patient H from the DC component of each of three-dimensional acceleration sensors 2a and 2b, a heart rate detector 8 for detecting a heart rate of the patient H from the AC component of the three-dimensional acceleration sensor 2a, a comprehensive assessment part 6 for performing a comprehensive assessment of the breathing movement, and a result output part 7 for outputting a result obtained by the comprehensive assessment part 6 to an external device (not shown) such as a personal computer.

In addition to the acceleration sensors 2a and 2b, the sleep diagnosis device 1 further includes a temperature sensor (not shown), such as a thermistor, for detecting a breathing movement by a patient's nose (that is, nose flow), a temperature sensor (not shown), such as a thermistor, for detecting a breathing movement by a patient's mouth (that is, mouth flow), a blood oxygen saturation measuring equipment (not shown) for measuring saturation of oxygen in blood (SPO2) of the patient H, and a sound collector (not shown) for measuring snores (tracheal sounds) of the patient H. The comprehensive assessment part 6 is configured to perform a comprehensive assessment (evaluation) of the breathing movement by using breathing movement information obtained by the breathing movement detector 4, posture information obtained by the posture detector 5, a heart rate obtained by the heart rate detector 8, and various information obtained by other sensors.

Hereinafter, the sleep diagnosis device 1 of this embodiment will be described in detail.

Figure 3A:
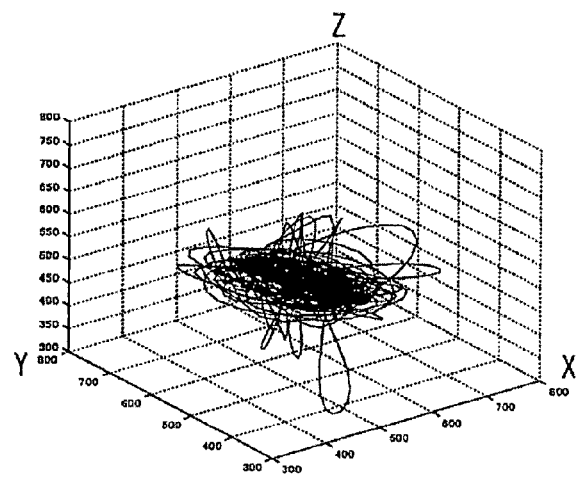
FIG. 3A is a view showing one example of the three-dimensional acceleration data obtained by the three-dimensional acceleration sensor.

Each acceleration sensor 2a and 2b is a three-dimensional acceleration sensor (a triaxial acceleration sensor) capable of detecting acceleration in three directions perpendicular to one another. For example, a piezoresistive type acceleration sensor using Micro Electro Mechanical Systems (MEMS), which is small and has low power consumption, can be used as such an acceleration sensor. By using such an acceleration sensor, it is possible to obtain an output (voltage level) corresponding to acceleration (three-dimensional acceleration) in three directions (X-axis direction, Y-axis direction, and Z-axis direction) perpendicular to one another as shown in FIG. 3A, and it is possible to use the output as three-dimensional acceleration data.

Figure 2A:
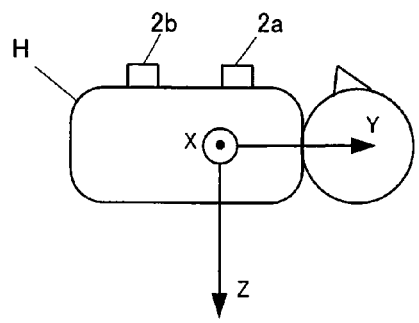
FIG. 2A is a view showing a state where a patient who wears acceleration sensors in the sleep diagnosis device of FIG. 1 is seen from a lateral side.
Figure 2B:
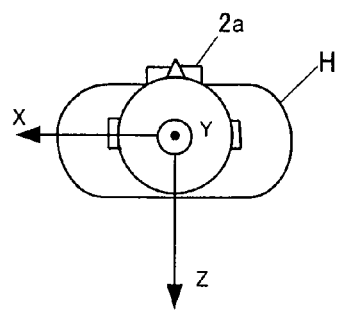
FIG. 2B is a view showing a state where the patient who wears acceleration sensors in the sleep diagnosis device of FIG. 1 is seen from a head side.

The acceleration sensor 2a is placed on a chest of the patient H as shown in FIG. 2A, and the acceleration sensor 2b is placed on a belly of the patient H as shown in FIG. 2A. As shown in FIGS. 2A and 2B, each acceleration sensor 2a and 2b is attached to the patient H so that a left-right direction (width direction) of the patient lying supine in a horizontal plane becomes the X-axis direction (a left shoulder side is a positive side and a right shoulder side is a negative side.), a body height direction of the patient H becomes the Y-axis direction (a head side is a positive side, and a foot side is a negative side.), and a thickness direction of the patient parallel to a normal line of the horizontal plane becomes the Z-axis direction (a back side is a positive side, and a front side is a negative side.).

Figure 4:
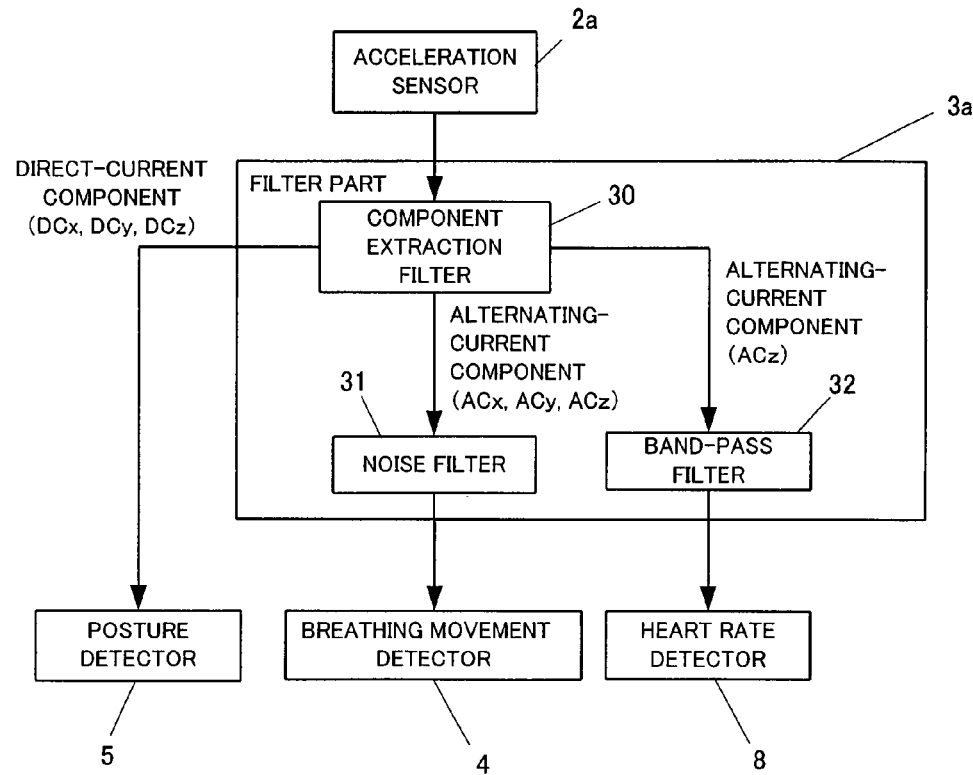
FIG. 4 is a block diagram of a filter part of the sleep diagnosis device of FIG. 1.

As shown in FIG. 4, the filter part 3a comprises a component extraction filter 30 for separating the output of the acceleration sensor 2a into the DC component and the AC component, a noise filter 31 for filtering out a high-frequency noise from the AC component extracted by the component extraction filter 30, and a band-pass filter 32 for filtering a Z-axial component ACz out of the AC component extracted by the component extraction filter 30. The DC component extracted by the component extraction filter 30 is transmitted to the posture detector 5, the AC component which passed through the noise filter 31 is transmitted to the breathing movement detector 4, and the AC component which passed through the band-pass filter 32 is transmitted to the heart rate detector 8.

As the noise filter 31, for example, a Bryant filter, which is often used in data processing of biomechanics, can be used. As the band-pass filter 32, a band-pass filter which passes an AC component in a range of 10 to 15 Hz can be used.

In this embodiment, although the output of the acceleration sensor 2a is separated into the DC component and the AC component, because the DC component is larger than the AC component, the output of the acceleration sensor may be directly used as the DC component.

The filter part 3b has a constitution in which the band-pass filter 32 is removed from the filter part 3a, so an explanation of the filter part 3b is skipped.

The breathing movement detector 4 detects a breathing movement of the patient by using the AC component of each acceleration sensor 2a and 2b obtained by each filter part 3a and 3b.

The breathing movement detector 4 is realized by software by using CPU and so on, and as shown in FIG. 1, the breathing movement detector 4 includes a one-dimensional converting means 4a for generating one-dimensional acceleration data from the three-dimensional acceleration data obtained by the three-dimensional acceleration sensors 2a and 2b, an inflection point detecting means 4b which detects inflection points of a variation of the one-dimensional acceleration data from the one-dimensional acceleration data generated by the one-dimensional converting means 4a, and a breathing movement calculating means 4c for calculating the breathing movement, such as a breathing rate, detection of apnea, and strength of the breath, of the patient by using the inflection points obtained by the inflection point detecting means 4b.

The one-dimensional converting means 4a of this embodiment comprises a principal axis calculating means 40 for calculating a principal axis of the variation of the acceleration (that is, a principal direction of the movement) from the three-dimensional acceleration data obtained by the three-dimensional acceleration sensors 2a and 2b, a one-dimensional data generating means 41 which generates one-dimensional acceleration data by projecting the three-dimensional acceleration data onto the principal axis calculated by the principal axis calculating means 40.

Figure 3B:
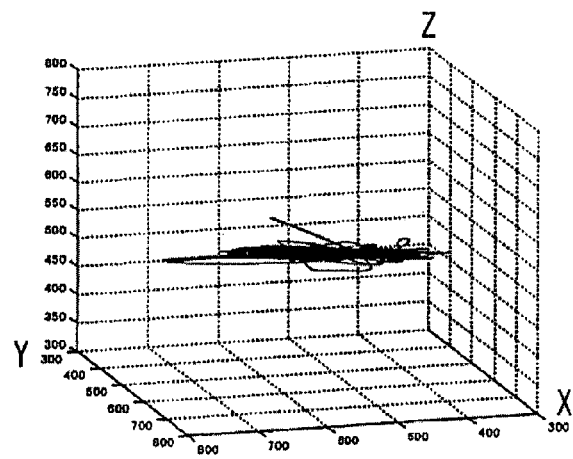
FIG. 3B is a view obtained by rotating FIG. 3A.

It is to be noted that, although the three-dimensional acceleration data obtained by the three-dimensional acceleration sensor put on the patient looks like a complex variation seemingly, it can be regarded as a movement in a flat surface when looking at it from a certain direction, as shown in FIG. 3B. That is, by calculating an approximate plane of the three-dimensional acceleration data, it is possible to convert the three-dimensional acceleration data into a two-dimensional acceleration data. The one-dimensional converting means 4a focuses attention on the above point, and it calculates the principal axis of the three-dimensional acceleration data to generate the one-dimensional acceleration data.

Figure 5:
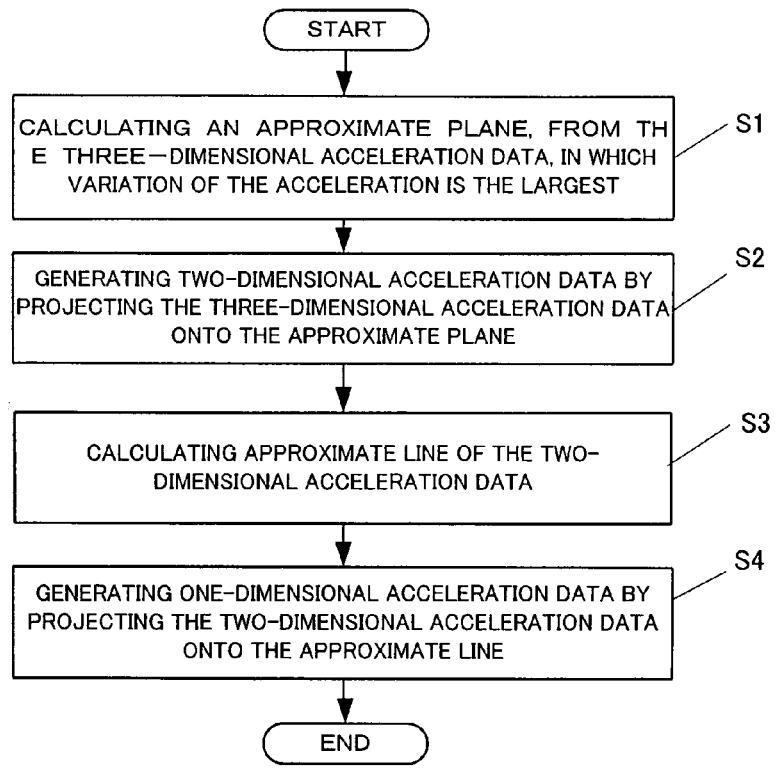
FIG. 5 is a flow chart for explaining a method for processing the data of the acceleration sensor in the sleep diagnosis device of FIG. 1.

Concretely speaking, as shown in a flow chart of FIG. 5, the principal axis calculating means 40 includes a step S1 for calculating an approximate plane, from the three-dimensional acceleration data, in which the variation of the acceleration is the largest, a step S2 for generating two-dimensional acceleration data by projecting the three-dimensional acceleration data onto the approximate plane, and a step S3 for calculating an approximate line of the two-dimensional acceleration data, and the one-dimensional data generating means 41 includes a step S4 which uses the approximate line obtained by the steps S1 to S3 as a principal axis and generates one-dimensional acceleration data by projecting the two-dimensional acceleration data on to the principal axis.

Hereinafter, the steps S1 to S4 will be described in detail.

In the step S1, a normal vector is calculated by using arbitrary points of the three-dimensional acceleration data. These points are at least three points, and it is preferable that these points are data arranged in time series. For example, if the arbitrary three points arranged in time series out of the three-dimensional acceleration data are represented as A1=(x1, y1, z1), A2=(x2, y2, z2), and A3=(x3, y3, z3), respectively, a normal vector of a plane passing through these points A1, A2, and A3 can be expressed by the following equation (1) by using the exterior product.

$$M = (A2 - A1) \times (A3 - A1)$$
$$= \begin{vmatrix} x & y & z \\ x2-x1 & y2-y1 & z2-z1 \\ x3-x1 & y3-y1 & z3-z1 \end{vmatrix}$$
$$= \begin{pmatrix} (y2-y1)(z3-z1) - (z2-z1)(y3-y1) \\ (z2-z1)(x3-x1) - (x2-x1)(z3-z1) \\ (x2-x1)(y3-y1) - (y2-y1)(x3-x1) \end{pmatrix} \quad (1)$$

If the number of the data of the three-dimensional acceleration data is n (n is an integer number), "n–2" normal vectors M can be obtained.

Then, an average of the normal vectors M obtained as above is calculated to seek a normal vector W=(xn, yn, zn) of an approximate plane, and then vectors U and V (where vector U≠vector V) each of which runs at right angles to the normal vector W can be calculated. For example, the vectors U and V can be expressed by the following equations (2) and (3), respectively.

$$U = (yn, -xn, 0) \quad (2)$$

$$V = (yn, zn*yn - xn, -yn^2) \quad (3)$$

In the step S2, a unit vector of each vector U, V, and W obtained by the step S1 is calculated, and a matrix T for converting an arbitrary point P=(px, py, pz) in a XYZ coordinate system into a point P'=(pu, pv, pw) in a UVW coordinate system is calculated based on the unit vector. Such a matrix T can be calculated as an inverse matrix of a matrix S (see the following equation 4) which converts a point P'=(pu, pv, pw) in the UVW coordinate system into a point P=(px, py, pz) in the XYZ coordinate system (see the following equation 5).

$$\begin{pmatrix} px \\ py \\ pz \end{pmatrix} = S \begin{pmatrix} pu \\ pv \\ pw \end{pmatrix} = \begin{pmatrix} ux & vx & wx \\ uy & vy & wy \\ uz & vz & yz \end{pmatrix} \begin{pmatrix} pu \\ pv \\ pw \end{pmatrix} \quad (4)$$

$$\begin{pmatrix} pu \\ pv \\ pw \end{pmatrix} = T \begin{pmatrix} px \\ py \\ pz \end{pmatrix} = \begin{pmatrix} ux & vx & wx \\ uy & vy & wy \\ uz & vz & yz \end{pmatrix}^{-1} \begin{pmatrix} px \\ py \\ pz \end{pmatrix} \quad (5)$$

By using the above matrix T, it is possible to calculate the point P' in the UVW coordinate system converted from the point P in the XYZ coordinate system (in other words, it is possible to calculate the point P' which is obtained by projecting the point P in the XYZ coordinate system onto the UVW coordinate system.), and it is possible to obtain a two-dimensional data (pu, pv) by ignoring the pw in the point P' (that is, by ignoring the W-axis, and regarding it as a plane having only the U-axis and V-axis.)

Figure 6A:
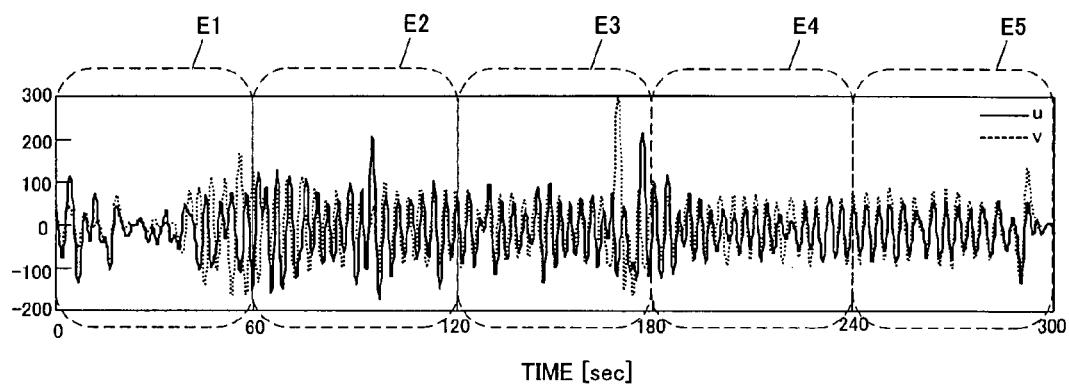
FIG. 6A is a view showing a two-dimensional acceleration data generated from the three-dimensional acceleration data in the sleep diagnosis device of FIG. 1.

Therefore, it is possible to obtain the two-dimensional acceleration data (u, v), as shown in FIG. 6A, by projecting the three-dimensional acceleration data in the XYZ coordinate system onto the UVW coordinate system by the matrix T and extracting only the points on the U-axis and the points on the V-axis out of the three-dimensional acceleration data projected onto the UVW coordinate system. In FIG. 6A, one example of the two-dimensional acceleration data in ten epochs is shown. In general, one epoch is any one of the thirty seconds, one minute, and two minutes, and in this embodiment, one epoch is thirty seconds.

Figure 7:
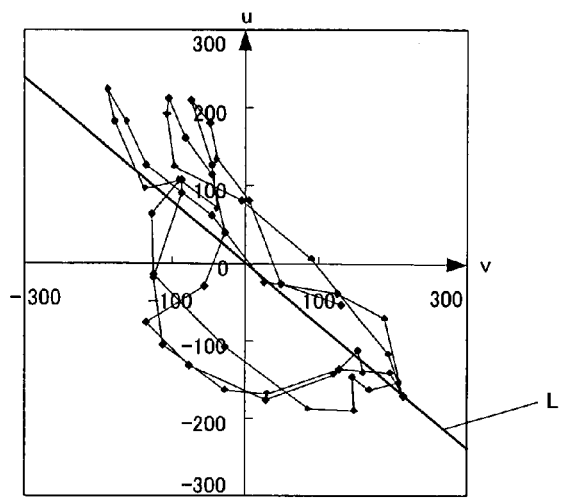
FIG. 7 is a view showing an approximate line calculated from the two-dimensional acceleration data.

In the step 3, as shown in FIG. 7, an approximate line L is calculated from the two-dimensional acceleration data (u,v) by using a least squares approximation.

As shown in FIG. 7, the approximate line L is represented as v=au+b, and when the two-dimensional acceleration data (u,v) in a predetermined time period (in this embodiment, in one epoch) is regarded as a set of $(u_1, v_1)$, $(u_2, v_2)$, $(u_3, v_3)$, . . . $(u_i, v_i)$, and n represents the number of the two-dimensional acceleration data, the above coefficients a and b are defined as the following equation (6).

$$\begin{pmatrix} \sum u_i^2 & \sum u_i \\ \sum u_i & n \end{pmatrix} \begin{pmatrix} a \\ b \end{pmatrix} = \begin{pmatrix} \sum u_i v_i \\ \sum v_i \end{pmatrix} \quad (6)$$

where i and n are both an integer, and n≦i.

Therefore, the coefficients a and b can be represented as the following equation (7) by calculating the inverse matrix.

$$\begin{pmatrix} a \\ b \end{pmatrix} = \begin{pmatrix} \sum u_i^2 & \sum u_i \\ \sum u_i & n \end{pmatrix}^{-1} \begin{pmatrix} \sum u_i v_i \\ \sum v_i \end{pmatrix} \quad (7)$$

Then, by using the coefficient a, a directional vector R=(s,t) of the approximate line v=au+b can be represented as the following equation (8).

$$(s, t) = \left( \frac{1}{\sqrt{a^2+1}}, \frac{a}{\sqrt{a^2+1}} \right) \quad (8)$$

The directional vector R=(s,t) obtained as above is used as a directional vector of the principal axis of the variation of the acceleration.

Figure 6B:
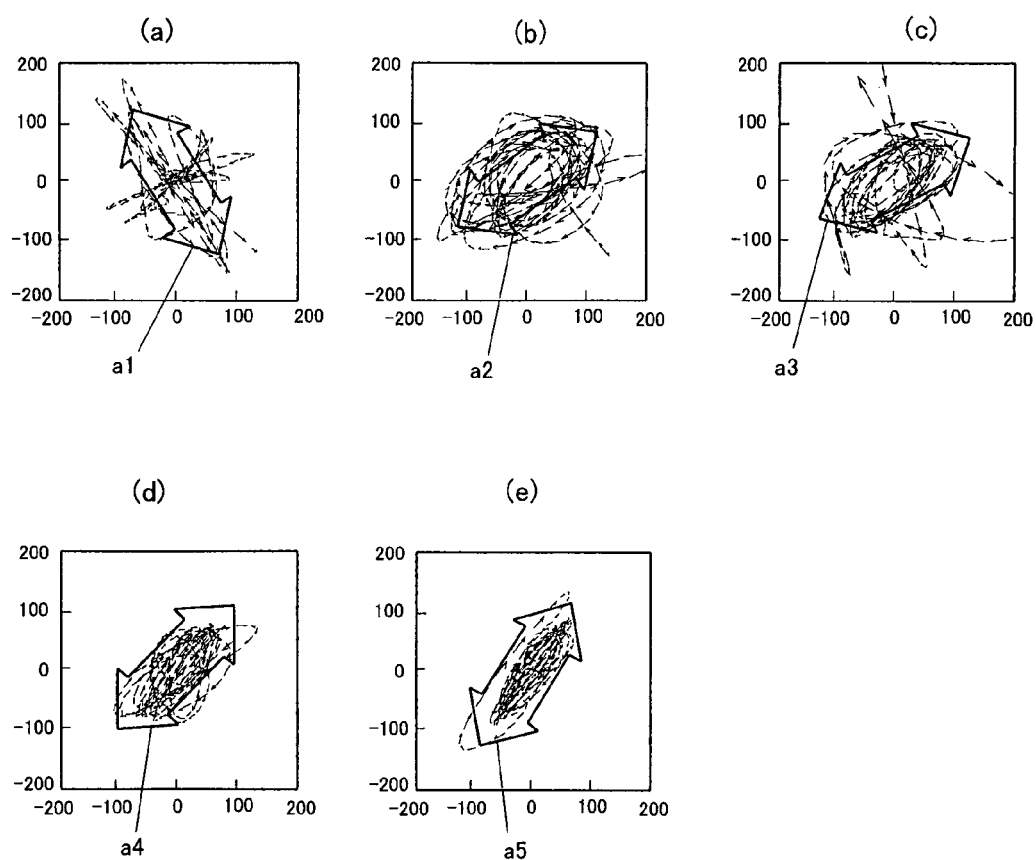
FIG. 6B is a view showing variations of the acceleration in periods shown by E1 to E5, respectively, in FIG. 6A.

By the way, a result that such a principal axis varies even in a short period of time of approximately one minute was obtained. For example, figures (a) to (e) of FIG. 6B show variations (loci) of the acceleration in the periods shown by E1 to E5 in FIG. 6A, respectively, and, arrows a1 to a5 in FIG. 6B show directions of the principal axis in the periods E1 to E5, respectively. As is clear from FIG. 6B, the locus of the acceleration changes greatly even in a short period of time of approximately one minute, and the direction of the principal axis also changes greatly. Therefore, it is preferable that the time interval of the calculation of the principal axis in the step 3 is shorter than that of the calculation of the approximate plane in the step S1 (in this embodiment, in the step S3, the principal axis is calculated every one epoch).

In the step S4, a one-dimensional acceleration data $r_i$, which is represented by the following equation (9), is generated by converting the two-dimensional acceleration data ($u_i$, $v_i$) into one dimension (that is, by projecting the two-dimensional acceleration data ($u_i$, $v_i$) onto the approximate line) by using the directional vector R obtained in the step S3.

$$r_i = s^* u_i + t^* v_i \quad (9)$$

Figure 8:
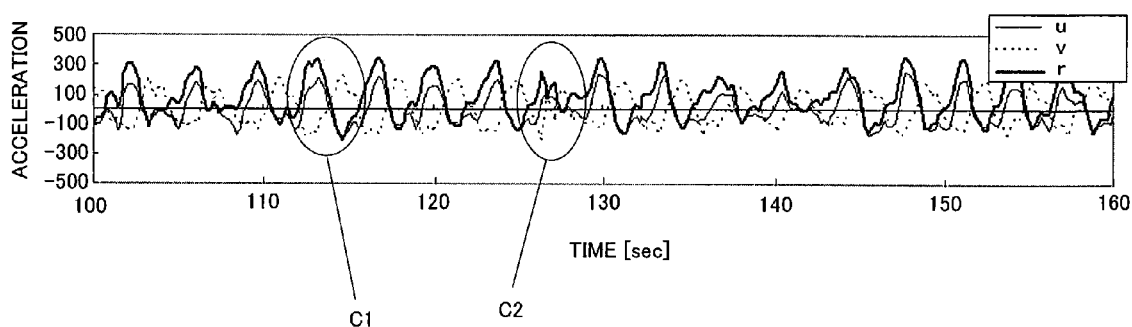
FIG. 8 is a view showing a one-dimensional acceleration data generated by a one-dimensional converting means comprising a principal axis calculating means and a one-dimensional data generating means.

As above, the one-dimensional acceleration data $r_i$ in a predetermined one epoch can be obtained, and by connecting the data in all epochs in chronological order one-dimensional acceleration data r, as shown in FIG. 8, can be obtained.

As shown in FIG. 8, the one-dimensional acceleration data r obtained by the one-dimensional converting means 4a of this embodiment has about the same number of waves as the two-dimensional acceleration data (u,v), and has the same width as the two-dimensional acceleration data (u,v), so it is conceivable that the three-dimensional acceleration data is properly reflected in the one-dimensional acceleration data. That is, it is possible to obtain the one-dimensional acceleration data in which the variation of the acceleration is accurately reflected by calculating the principal axis of the variation of the acceleration from the three-dimensional acceleration data and projecting the multidimensional acceleration data onto the principal axis, as the one-dimensional converting means 4a of this embodiment.

The one-dimensional acceleration data generated by the one-dimensional converting means 4a as above is outputted to the inflection point detecting means 4b.

The inflection point detecting means 4b detects inflection points of the variation of the one-dimensional acceleration data from the one-dimensional acceleration data generated by the one-dimensional converting means 4a, and it detects the inflection points having an intensity difference between the inflection points larger than a predetermined threshold value out of the detected inflection points as effective inflection points.

The inflection point detecting means 4b includes an inflection point detecting step for detecting inflection points of the variation of the one-dimensional acceleration data, an effective inflection point selecting step for selecting the inflection points which can be used effectively for detecting the breathing movement out of the inflection points detected by the inflection point detecting step as the effective inflection points, and an effective inflection point alignment step for aligning the effective inflection points obtained by the effective inflection point selecting step.

The inflection point detecting step judges a point at which the sign (plus and minus sign) of the differential value of the one-dimensional acceleration data reverses to be an inflection point. When it judges a point to be the inflection point, it memorizes a value of the acceleration data (it is regarded as an intensity of the inflection point.) at the point, a time of the point, and a type of the inflection point (a convex inflection point or a concave inflection point) as inflection points P1(j) (where j is an integer).

Figure 9A:
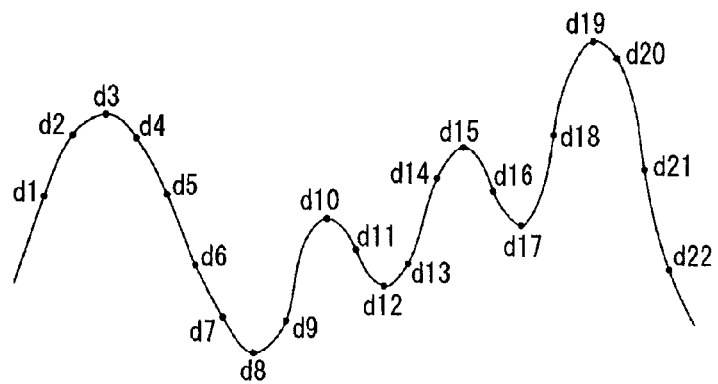
FIG. 9A is a view for explaining a process to select an effective inflection point from the one-dimensional acceleration data.
Figure 9B:
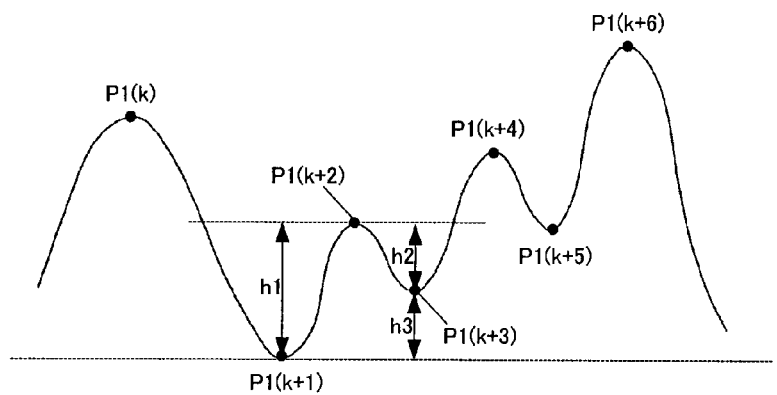
FIG. 9B is a view for explaining a process to select an effective inflection point from the one-dimensional acceleration data.

For example, in a case of one-dimensional acceleration data having points d1 to d22 as shown in FIG. 9A, inflection points P1(k) to P1(k+6) can be obtained as shown in FIG. 9B by the inflection point detecting step.

The effective inflection point selecting step selects the effective inflection points out of the inflection points P1(j) detected by the inflection point detecting step, and it makes effective inflection points P2(l), where l is an integer.

In order to determine the effective inflection point, a primary judgment step, which temporary judges the effective inflection point by whether a width of a targeted inflection point (that is, a difference of a value of the acceleration data between the targeted inflection point and an inflection point judged to be the effective inflection point last, or in other words, intensity difference of the inflection points) is larger than a predetermined threshold value dA or not, and a secondary judgment step, which is activated when it was judged that the width of the targeted inflection point was less than the threshold value dA and judges which inflection point is suitable for the effective inflection point, the targeted inflection point or the inflection point judged to be the effective inflection point last, are performed.

For example, in FIG. 9B, in a case where the targeted inflection point is P1(k+2) and the inflection point judged to be the effective inflection point last is P1(k+1), the width of the targeted inflection point P1(k+2), that is, the intensity difference h1 between the targeted inflection point P1(k+2) and the inflection point P1(k+1) judged to be the effective inflection point last, is compared with the predetermined threshold value dA in the primary judgment step, and if the intensity difference h1 is larger than the threshold value dA, the targeted inflection point P1(k+2) is memorized as the effective inflection point. Then, the inflection point P1(k+3) is targeted, and the intensity difference h2 between the targeted inflection point P1(k+3) and the inflection point P1(k+2) judged to be the effective inflection point last is compared with the predetermined threshold value dA, and if the intensity difference h2 is less than the threshold value dA, the secondary judgment step is activated.

In the secondary judgment step, the intensity difference H1 between the effective inflection point just before the effective inflection point judged last and the effective inflection point judged last is compared with the intensity difference H2 between the effective inflection point just before the effective inflection point judged last and the targeted inflection point, and if the intensity difference H1 is greater than the intensity difference H2, the targeted inflection point is excluded from the candidates of the effective inflection point, and on the other hand, if the intensity difference H1 is less than the intensity difference H2, the targeted inflection point is adopted as the effective inflection point as a substitute for the effective inflection point judged last.

For example, in the above case, when the secondary judgment step is activated, the intensity difference h1 between the effective inflection point P1(k+1) just before the effective inflection point judged last and the effective inflection point P1(k+2) judged last is compared with the intensity difference h3 between the effective inflection point P1(k+1) just before the effective inflection point judged last and the targeted inflection point P1(k+3). Because, in this case, the intensity difference h1 is greater than the intensity difference h3, the targeted inflection point P1(k+3) is excluded from the candidates of the effective inflection point. If the intensity difference h1 is less than the intensity difference h3, the targeted inflection point P1(k+3) is adopted as the effective inflection point as a substitute for the effective inflection point P1(k+2) judged last.

Figure 9C:
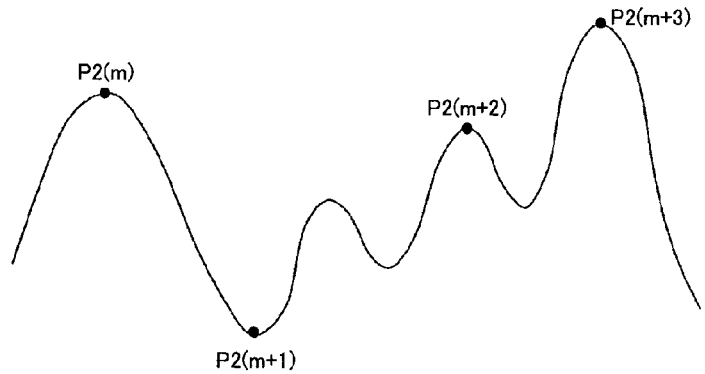
FIG. 9C is a view for explaining a process to select an effective inflection point from the one-dimensional acceleration data.
Figure 9D:
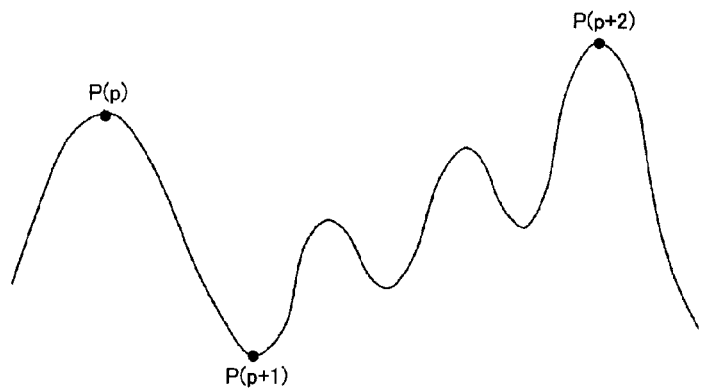
FIG. 9D is a view for explaining a process to select an effective inflection point from the one-dimensional acceleration data.

In the case of FIG. 9B, as shown in FIG. 9C, the effective inflection points P2(m) to P2(m+3) are selected out of the inflection points P1(k) to P1(k+6) by the effective inflection point selecting step.

For information, as the predetermined threshold value dA, a value defined by American Academy of Sleep Medicine (AASM) is used. Concretely speaking, one half of the mean amplitude of the one-dimensional acceleration data in two minutes just before the epoch in which the effective inflection point is selected is used as the threshold value dA.

In the effective inflection point alignment step, if peaks or valleys appear consecutively in the effective inflection points P2($l$), only the effective infection point which has the largest intensity difference with respect to the effective inflection point just before them is saved so that the peak and the valley appear alternately.

For example, in FIG. 9C, by the effective inflection point alignment step, the effective inflection point P2($m$+2) is removed, and the effective inflection points P2($m$), P2($m$+1), and P2($m$+3) are decided as the effective inflection points P(p), P(p+1), and P(p+2) (where p is an integer).

The effective inflection points P(p) obtained by the inflection point detecting means 4b is transmitted to the breathing movement calculating means 4c.

The breathing movement calculating means 4c is for calculating various information necessary for diagnosing sleep using the effective inflection points P(p), and it includes a breathing rate calculating means 42 for calculating the breathing rate of the patient, an apnea detecting means 43 for detecting an apnea interval, an apnea period detecting means 44 for getting a stop time of the apnea interval as a breathing start time, and a breathing strength calculating means 45 for calculating strength of the breath.

Figure 10:
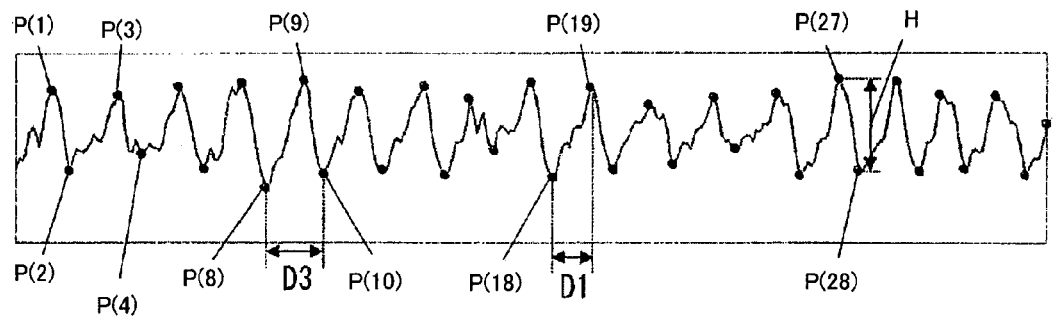
FIG. 10 is a view for explaining a method for detecting the breathing movement from the effective inflection point in the sleep diagnosis device of FIG. 1.

The breathing rate calculating means 42 calculates a breathing rate per unit of time (in this embodiment, per minute) by using a time difference between a certain convex inflection point and the next convex inflection point, or a time difference between a certain concave inflection point and the next concave inflection point, out of the effective inflection points P(p) detected by the inflection point detecting means 4b. For example, in FIG. 10, it calculates a time difference D3 [sec] between an effective inflection point P(8), which is a certain concave inflection point, and an effective inflection point P(10), which is the next concave inflection point, and then it calculates 60/D3 to obtain the breathing rate per unit of time.

The apnea detecting means 43 detects the interval between adjacent effective inflection points as the apnea interval if the time difference between the adjacent effective inflection points is greater than a criterion value. For example, in FIG. 10, the apnea detecting means 43 calculates the time difference D1 between the adjacent effective inflection point P(18) and the effective inflection point P(19), and if the time difference D1 is greater than a criterion value for the judgment of the apnea interval, it detects the interval between the effective inflection points P(18) and P(19) as the apnea interval. Furthermore, the apnea detecting means 43 counts a frequency of the apnea interval detected as above.

The apnea period detecting means 44 gets a start time of the apnea interval as a breathing stop time when the apnea detecting means 43 detected the apnea interval, and it gets a stop time of the apnea interval as a breathing start time. For example, if the interval between the effective inflection point P(18) and the effective inflection point P(19) is detected as the apnea interval, the apnea period detecting means 44 obtains the time of the effective inflection point P(18) as the breathing stop time and it obtains the time of the effective inflection point P(19) as the breathing start time.

The breathing strength calculating means 45 calculates the strength of the breath by using intensity difference between the adjacent effective inflection points. For example, in FIG. 10, the breathing strength calculating means 45 calculates the intensity difference H between the effective inflection points P(27) and P(28) as an indicator of the strength of the breath at the effective inflection point P(28). The strength of the breath which is obtained as above is calculated at every effective inflection point P(p), and then the average of the strength of the breath is calculated after the strength of the breath is calculated at every inflection point P(p), and the average is used for calculating the above threshold value dA in the next epoch.

The breathing rate, the apnea interval, the strength of the breath, and so on of the patient calculated as above are transmitted to the comprehensive assessment part 6.

Reverting to FIG. 1, the posture detector 5 calculates a trunk angle θ and a sleeping posture angle f of the patient from the DC component of each acceleration sensor 2a and 2b extracted by each filter part 3a, 3b, and transmits the calculated posture information to the comprehensive assessment part 6.

Figure 11A:
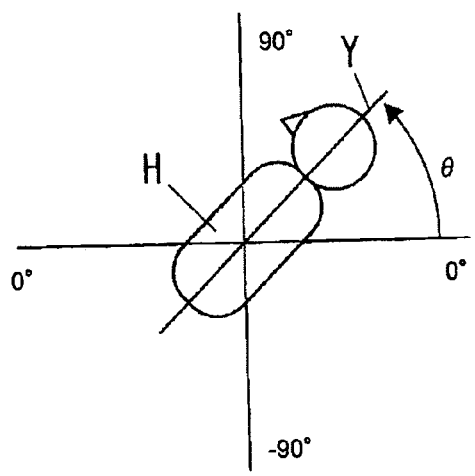
FIG. 11A is a view for explaining a trunk angle.
Figure 11B:
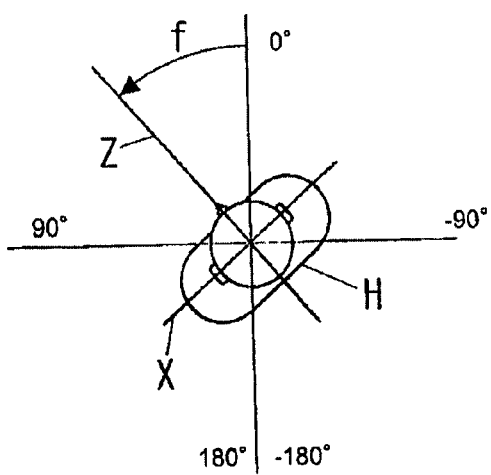
FIG. 11B is a view for explaining a sleeping posture angle.

For information, as shown in FIG. 11A, the trunk angle means an angle θ (−180°≦θ≦180°) between the Y-axis direction and the horizontal direction, and as shown in FIG. 11B, the sleeping posture angle means an angle f (−180°≦f≦180°) between the Z-axis direction and the normal direction of the horizontal plane.

Hereinafter, the method for calculating the trunk angle θ and the sleeping posture angle f from the DC component of each acceleration sensor 2a and 2b will be explained. Because the method for calculating the trunk angle θ and the sleeping posture angle f is common to the acceleration sensor 2a and the acceleration sensor 2b, in the following explanation, only the case of the acceleration sensor 2a will be described.

First, a unit vector of the gravitational acceleration is calculated from each component of the DC component of the acceleration sensor 2a obtained by the filter part 3a in respective axial directions (the X-axis direction, the Y-axis direction, and the Z-axis direction). When the outputs (voltage values) of each component of the DC component of the acceleration sensor 2a in respective axial directions are represented as (DCx, DCy, DCz), and the output (the voltage value) of the acceleration sensor 2a corresponding to the gravitational acceleration (about 9.8 m/s$^2$) is represented as G, the unit vector of the gravitational acceleration GA=(Gx, Gy, Gz) can be obtained by the acceleration sensor 2a, and the values of the Gx, Gy, and Gz are represented by the following equation (10).

$$Gx = \frac{DCx}{G}$$
$$Gy = \frac{DCy}{G}$$
$$Gz = \frac{DCz}{G}$$
(10)

By using the unit vector GA=(Gx, Gy, Gz) obtained by the above calculations, the trunk angle θ can be represented by the following equation (11):

$$\theta = -\arcsin(Gy) * \left(\frac{180}{pi}\right)$$
(11)

where pi is a ratio of the circumference of a circle to its diameter.

If the posture detector 5 judges that the patient is in a recumbent position (or, Gy≈0) from the trunk angle θ, it then calculates the sleeping posture angle f.

The sleeping posture angle f is divided into cases according to plus and minus of each Gz and Gx. When Gz≧0, it is represented by the following equation (12).

$$f = \arcsin(Gx) * \left(\frac{180}{pi}\right) \quad (12)$$

In a case where Gz<0, when Gx≧0, the sleeping posture angle f is represented by the following equation (13), and when Gx<0, it is represented by the following equation (14).

$$f = 180 - \arcsin(Gx) * \left(\frac{180}{pi}\right) \quad (13)$$

$$f = -180 - \arcsin(Gx) * \left(\frac{180}{pi}\right) \quad (14)$$

As mentioned above, the posture detector 5 can calculate the trunk angle θ and the sleeping posture angle f by using the DC component (DCx, DCy, DCz) of each acceleration sensor 2a, 2b, and it can detect the posture of the patient H accurately by the values of the trunk angle θ and the sleeping posture angle f.

Figure 12:
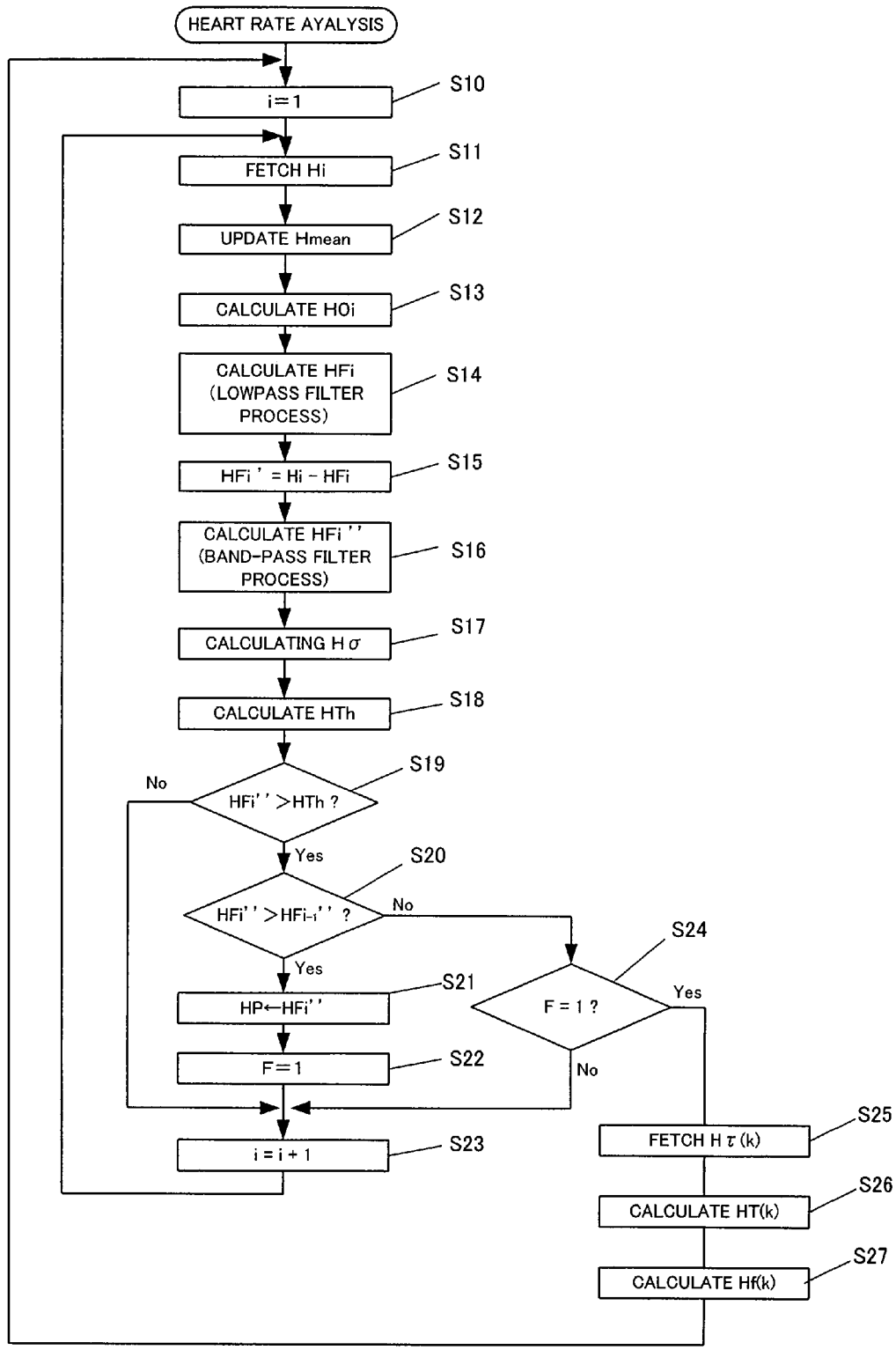
FIG. 12 is a flow chart for explaining a method for detecting a heart rate in the sleep diagnosis device of FIG. 1.

The heart rate detector 8 filters a component ACz of the AC component of the three dimensional acceleration sensor 2a in the z-axis direction by the band-pass filter 32, and it calculates the inverse of the peak period of the ACz to detect the heart rate of the patient. FIG. 12 shows a flow chart for explaining an analysis method of the heat rate.

First, in a step S10, the heart rate detector 8 initializes a variable i, which represents timing, to 1, and since then, in a step S11, it fetches the component ACz of the AC component in the z-axis direction every 5 msec, and it considers the component ACz as a value $H_i$ of this time. In a step S12, a moving average value $H_{mean}$ of the data of predetermined sampling numbers is updated, and in a step S13, the moving average value $H_{mean}$ is subtracted from the value $H_i$ to shift the zero point. The value obtained in the step S13 is denoted by a correction value $H0_i$. In a step S14, a lowpass filter process of 10 Hz is performed with respect to the correction value $H0_i$, and the result value is denoted by a filtered value $HF_i$. In a step S15, the filtered value $HF_i$ is subtracted from the value $H_i$, and as a result, a filtered value $HF_i'$ processed by a highpass filter of 10 Hz or more is obtained. In a step S16, a lowpass filter process of 15 Hz is performed with respect to the filtered value $HF_i'$, and the result value obtained by the band-pass filter process is denoted by a filtered value $HF_i''$.

After the filtering process is performed as above in the steps S11 to S16, a standard deviation Hs of the data of predetermined sampling numbers is updated in a step S17, and a threshold value HTh is calculated by adding the standard deviation Hs to a predetermined threshold value Th.

In a step S19, it is judged that whether the filtered value $HF_i''$ of this time is greater than the threshold value HTh or not, and if it is greater, the filtered value $HF_i''$ is further compared with the filtered value $HF_{i-1}''$ of the last time in a step S20, and if it is greater, a peak value HP is updated to the filtered value $HF_i''$ of this time in a step S21, and a flag F for indicating that the peak value HP exists is set to 1 in a step S22. In the step S19, if the filtered value $HF_i''$ of this time is less than or equal to the threshold value HTh, or if the present step is in the step S22, the step proceeds to a step S23, and the variable i is incremented by one, and the step returns to the step S11, and then the next measurement of the acceleration is fetched.

In the step S20, if the filtered value $HF_i''$ of this time is less than or equal to the filtered value $HF_{i-1}''$, the step proceeds to a step S24, and there, it is judged that whether the flag F is set to 1 or not, and if not, because it can be judged that the acceleration decreases monotonously, the step returns to the step S11 through the step S23, and the next measurement of the acceleration is fetched.

On the other hand, in the step S24, if the flag is set to 1, because it can be judged that the acceleration is decreasing after the peak of the acceleration was detected, timing Hτ(k) at which the peak value HP was detected is fetched in a step S25, and a period HT(k) from the timing Hτ(k−1) when the last peak value HT was detected to the timing Hτ(k) is calculated in a step S26. Then, the inverse of the period HT(k) is calculated in a step S27, whereby the heart rate Hf(k) per minute of this time can be obtained. Then, the step returns to the step S10 to detect the next peak.

The comprehensive assessment part 6 is constituted by a micro computer and so on, and it performs a comprehensive assessment (evaluation) of apnea by using outputs from the breathing movement detector 4, the posture detector 5, the heart rate detector 8, the temperature sensor, the blood oxygen saturation measuring equipment, the sound collector, and so on.

For example, the comprehensive assessment part 6 calculates the number of the apnea interval, the time, and a duration thereof based on the presence or absence of the halt of the nose flow obtained by the temperature sensor for detecting the nose flow, and it judges apnea by using the respiration information by the nose flow, the respiration information by the mouth flow, the breathing movement information obtained by the breathing movement detector 4, and the SPO2 information obtained by the blood oxygen saturation measuring equipment.

The judgment of the apnea is performed by whether both the nose flow and the mouth flow have stopped or not, and if both the nose flow and the mouth flow have stopped, it is judged to be apnea. If it is judged to be apnea, a type of the apnea is determined from the information obtained by the breathing movement detector 4. That is, if the breathing movements of both the chest (that is, the acceleration sensor 2a) and the belly (that is, the acceleration sensor 2b) have stopped, it is determined to be central apnea, which results from a stop of a respiration command from the brain. Or, if there is a disturbance in the waveforms of the breathing movements of the chest and the belly, or if there is a phase lag between the breathing movements of the chest and the belly, it is determined to be obstructive apnea, which results from airflow obstruction. Or, if the breathing movements of the chest and the belly start again after the breathing movements of the chest and the belly stopped and before the nose flow and the mouth flow start again, it is determined to be mixed apnea.

Furthermore, if it is judged to be apnea, the posture information of the patient H in the apnea interval is added to the apnea information. By this information, it becomes possible to judge that the patient is in a waking state or a sleeping state, and it becomes possible to assess the possibility of reducing the appearance of apnea by a sleeping direction (that is, by lying on his back, lying on his side, and so on).

Furthermore, the number of the apnea (infrequent respiration) per hour, that is AHI, is calculated by dividing the number of each apnea (central apnea, obstructive apnea, and mixed apnea) by sleeping hours of the patient H, and the number of reduction of SPO2 per hour, that is ODI, is calculated by dividing the number of reduction of SPO2 by the sleeping hours of the patient H. And, based on the values of the AHI and the ODI, a degree of severity of the sleep apnea syndrome is assessed.

As to the sleeping hours, cumulative hours of periods in which it is judged that the patient H is in the sleeping posture by the posture detector 5 out of the data acquisition period, that is, the period in which the sleeping posture angle f is calculated, is used as the sleeping hours.

Or, a non-REM sleep state may be estimated by using the heart rate and the variations of the outputs of the accelerations sensors 2a and 2b, and the data acquisition period except for the periods in which the patient is in wakefulness may be used as the sleeping hours.

The result obtained by the comprehensive assessment part 6 and the information of the breathing movement (that is, the apnea interval, the breathing stop time, the breathing start time, the strength of the breath, and the breathing rate per unit of time of the patient H) obtained by the breathing movement detector 4, and the outputs from other sensors and devices are transmitted to the result output part 7.

The output part 7 outputs the result obtained by the comprehensive assessment part 6 to an external device.

As mentioned above, because it is possible for the sleep diagnosis device 1 of this embodiment to detect the posture (sleeping posture), the breathing movement, and the heart rate of the patient from the three-dimensional acceleration sensor, it is possible to reduce the number of the sensors, whereby it is possible to lessen a burden of the patient. Furthermore, as mentioned above, the sleep diagnosis device of this embodiment can detect the breathing movement of the patient accurately by using the three-dimensional acceleration sensor.

Although the one-dimensional converting means 4a of this embodiment is constituted by the principal axis calculating means 40 and the one-dimensional data generating means 41 in order to obtain one-dimensional acceleration data from three-dimensional acceleration data, the one-dimensional converting means 4a may be constituted so that it calculates norm of the three-dimensional acceleration data and uses the norm as the one-dimensional acceleration data.

That is, when three-dimensional acceleration data is represented by (ax, ay, az) where ax is acceleration data in the x-axis direction, ay is acceleration data in the y-axis direction, and az is acceleration data in the z-axis direction, the norm of the three-dimensional acceleration data is defined as $(ax^2+ay^2+az^2)^{1/2}$, and the one-dimensional converting means may use such a norm as the one-dimensional acceleration data.

However, when the norm is used, a problem may occur according to circumstances. Hereinafter, an issue arising when the norm is used as the one-dimensional acceleration data will be explained. In the following explanation, for the sake of simplification of the explanation, only the acceleration data ax in the x-axis direction and the acceleration data ay in the y-axis direction out of the three-dimensional acceleration data are treated, and $(ax^2+ay^2)^{1/2}$ is used as the value of the norm.

For example, in a case where the acceleration data ax in the x-axis direction and the acceleration data ay in the y-axis direction each has a waveform which oscillates around the zero, the number of concavities and convexities (namely, waves) in the waveform of the norm N (that is, the waveform of the one-dimensional acceleration data N) is approximately twice as many as each ax and ay. That is, in the case of the waveform mentioned above, if the norm is used to convert the acceleration data into one dimension, it becomes difficult to grasp the behavior of the two-dimensional acceleration data. And, as is clear from the waveform of the norm N, the amplitude of the waveform of the norm N becomes smaller than respective waveforms of ax and ay, so the influence of the oscillation by the noise and so on may become larger.

Figure 13A:
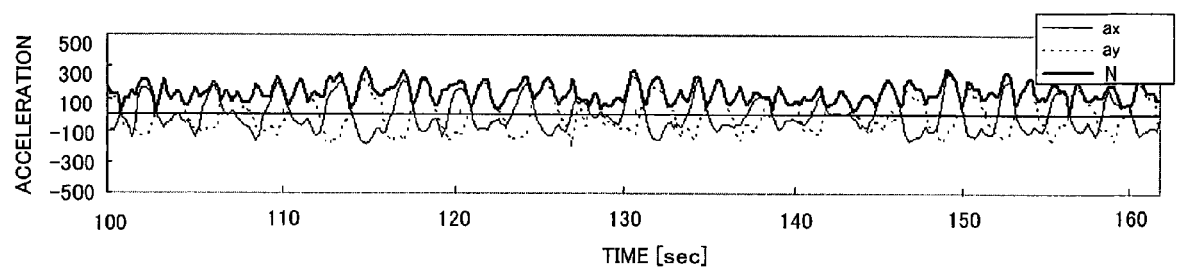
FIG. 13A is a view showing one example of the one-dimensional acceleration data generated by another one-dimensional converting means in the sleep diagnosis device of FIG. 1.
Figure 13B:
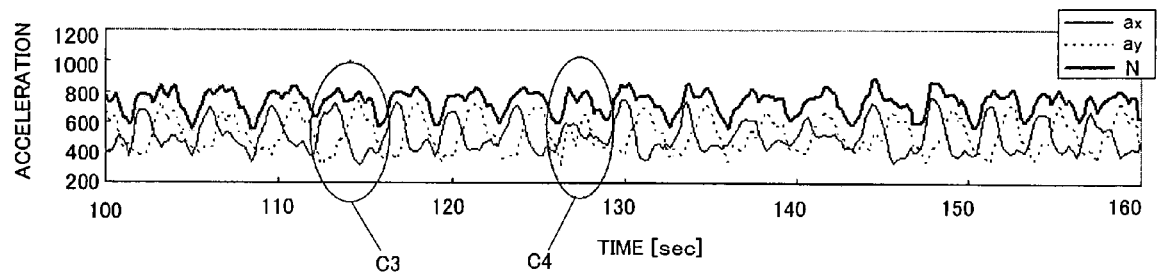
FIG. 13B is a view showing another example of the one-dimensional acceleration data generated by another one-dimensional converting means.

Furthermore, in a case where the acceleration data ax in the x-axis direction and the acceleration data ay in the y-axis direction each has a waveform which oscillates in a positive area as shown in FIG. 13 and the waveform of the acceleration data ax in the x-axis direction and the waveform of the acceleration data ay in the y-axis direction are out of phase with each other, the amplitude of the norm N changes little in a time period over which the acceleration data ax and the acceleration data ay each has a large amplitude as shown by C3 in FIG. 13B and in a time period over which the acceleration data ax and the acceleration data ay each has a small amplitude as shown by C4 in FIG. 13B, which indicates that the norm N does not reflect the magnitude of the actual movement. This is because the norm is a value evaluated by a distance from an origin point (in other words, magnitude of the acceleration data ax and the acceleration data ay at each instant of time), and when the waveform of the acceleration data ax in the x-axis direction and the waveform of the acceleration data ay in the y-axis direction are out of phase with each other in a time period over which the acceleration data ax and the acceleration data ay each has a large amplitude as shown by C3, these waveforms cancel each other out, so the amplitude of the norm becomes small.

As mentioned above, when three-dimensional acceleration data is converted into one dimension by using the norm, a variation of the three-dimensional acceleration data may not be reflected in the one-dimensional acceleration data according to circumstances.

On the other hand, as show in FIG. 8, in the one-dimensional acceleration date obtained by the one-dimensional converting means 4a of this embodiment, the number of concavities and convexities (namely, waves) does not approximately double even when the two-dimensional acceleration data (u,v) has a waveform which oscillates around the zero, and the three-dimensional acceleration data is accurately reflected in the one-dimensional acceleration data. Furthermore, the amplitude of the waveform of the one-dimensional acceleration data does not become smaller than the waveform of the original acceleration data.

Still furthermore, as a time period shown by C1 in FIG. 8, even when the waveforms of the two-dimensional acceleration data (u,v) are out of phase with each other, the amplitude thereof does not become smaller as the time period shown by C3 of FIG. 13B. Therefore, as shown by C1 in FIG. 8, the time period over which the amplitude of each waveform of the two-dimensional acceleration data (u,v) is large and the time period over which the amplitude thereof is small as shown by C2 are accurately reflected in the amplitude of the one-dimensional acceleration data r.

As mentioned above, although the one-dimensional converting means 4a may use the norm of the three-dimensional acceleration data as the one-dimensional acceleration data, it is preferable that the one-dimensional converting means 4a is constituted by the principal axis calculating means 40 and the one-dimensional data generating means 41 as this embodiment.

Although, in this embodiment, the principal axis calculating means 40 is configured so that it calculates the approximate plane based on the three-dimensional acceleration data and generates the two-dimensional acceleration data by projecting the three-dimensional acceleration data onto the approximate plane and calculates the approximate line based on the two-dimensional acceleration data, and the one-dimensional data generating means 41 is configured so that it generates the one-dimensional acceleration data by projecting the two-dimensional acceleration data onto the approximate line calculated in the principal axis calculating process, the principal axis calculating means 40 and the one-dimensional data generating means 41 each are not limited to the above-mentioned constitution. For example, the principal axis calculating means may be configured so that it calculates the approximate line by using the three-dimensional acceleration data, and the one-dimensional data generating means may be configured so that it uses the approximate line calculated by the principal axis calculating means as the principle axis, and it calculates the one-dimensional acceleration date by projecting the tree-dimensional acceleration data onto the principle axis.

Furthermore, the sleep diagnosis device 1 of this embodiment may have a step detecting means for calculating steps that a patient makes by using the outputs of the three-dimensional acceleration sensors 2a and 2b. The steps that the patient makes can be calculated by using the respective DC components DCx, DCy, DCz of the three-dimensional acceleration sensors 2a and 2b as the number of times that a composite value $(DCX^2+DCy^2+DCZ^2)^{1/2}$ exceeds a predetermined threshold value. By providing the step detecting means, it is possible to obtain data of the number of times that the patient goes to a bathroom and the number of times that the patient turned out, which could be obtained by only doctor's questions in the conventional art, whereby it becomes possible to grasp the quality of the sleep comprehensively by a seated position and the number of times of the steps.

Although, in this embodiment, the heart rate of the patient is detected by the heart rate detector 8, the heart rate may be detected by using a pulse meter and so on.

As mentioned above, as many apparently widely different embodiments of this invention may be made without departing from the spirit and scope thereof, it is to be understood that the invention is not limited to the specific embodiments thereof except as defined in the appended claims.

The invention claimed is:

1. A sleep diagnosis device comprising:
a three-dimensional acceleration sensor,
a posture detecting means for detecting a posture of a patient from a DC component of said three-dimensional acceleration sensor, and
a breathing movement detecting means for detecting a breathing movement of the patient from an AC component of said three-dimensional acceleration sensor,
wherein said breathing movement detecting means includes:
a one-dimensional converting means for generating one-dimensional acceleration data from the three-dimensional acceleration data obtained by said three-dimensional acceleration sensor;
an inflection point detecting means for detecting inflection points of a variation of said one-dimensional acceleration data from the one-dimensional acceleration data generated by said one-dimensional converting means; and
a breathing movement calculating means for calculating the breathing movement of the patient from the inflection points of the variation of the one-dimensional acceleration data obtained by said inflection point detecting means.

2. The sleep diagnosis device as set forth in claim 1, wherein
said one-dimensional converting means comprises:
a principal axis calculating means for calculating a principal axis of the variation of the acceleration from the three-dimensional acceleration data obtained by said three-dimensional acceleration sensor, and
a one-dimensional data generating means for generating the one-dimensional acceleration data by projecting the three-dimensional acceleration data onto the principal axis calculated by said principal axis calculating means.

3. The sleep diagnosis device as set forth in claim 2, wherein said principal axis calculating means is configured to calculate an approximate plane from the three-dimensional acceleration data and to generate a two-dimensional acceleration data by projecting the three-dimensional acceleration data onto the approximate plane and to calculate an approximate line from the two-dimensional acceleration data,
said one-dimensional data generating means being configured to use the approximate line calculated by said principal axis calculating means as a principal axis and to generate the one-dimensional acceleration data by projecting the two-dimensional acceleration data onto the principal axis.

4. The sleep diagnosis device as set forth in claim 2, wherein said principal axis calculating means is configured to calculate an approximate line by using the three-dimensional acceleration data,
said one-dimensional data generating means being configured to use the approximate line calculated by said principal axis calculating means as a principal axis and to generate the one-dimensional acceleration data by projecting the three-dimensional acceleration data onto the principal axis.

5. The sleep diagnosis device as set forth in claim 1, wherein
said breathing movement calculating means includes a breathing rate calculating means for calculating a breathing rate of the patient per unit of time by using a time difference between a certain convex inflection point and the next convex inflection point or a time difference between a certain concave inflection point and the next concave inflection point, out of the inflection points of the variation of the one-dimensional acceleration data.

6. The sleep diagnosis device as set forth in claim 1, wherein
said breathing movement calculating means includes an apnea detecting means for detecting an interval between adjacent inflection points of the variation of the one-dimensional acceleration data as an apnea interval if a time difference between the adjacent inflection points is greater than a criterion value.

7. The sleep diagnosis device as set forth in claim 6, wherein said breathing movement calculating means further includes an apnea period detecting means for getting a start time of the apnea interval as a breathing stop time and get a stop time of the apnea interval as a breathing start time when said apnea detecting means detects the apnea interval.

8. The sleep diagnosis device as set forth in claim 1, wherein
said breathing movement detecting means includes a breathing strength calculating means for calculating strength of a breath by using the intensity difference between adjacent inflection points of the variation of the one-dimensional acceleration data.

9. The steep diagnosis device as set forth in claim 1, wherein said posture detecting means calculates a trunk angle of the patient from each component DCy and DCz of the DC component of said three acceleration sensor in a y-axis and a z-axis directions, and calculates a sleeping posture angle of the patient from each component DCx and DCz of the DC component of the three acceleration sensor in an x-axis and a z-axis directions, when the x-axis direction is defined as a left-right direction of the patient and the y-axis direction is defined as a body height direction of the patient and the z-axis direction is defined as a thickness direction of the patient.

10. The sleep diagnosis device as set forth in claim 1, further comprises
 a heart rate detecting means for detecting a heart rate of the patient from the AC component of said three-dimensional acceleration sensor.

11. The sleep diagnosis device as set forth in claim 10, wherein
 said heart rate detecting means detects the heart rate of the patient by filtering a component ACz of the AC component of the three dimensional acceleration sensor in a z-axis direction by a band-pass filter and calculating an inverse of a peak period of the filtered component ACz.

* * * * *